United States Patent [19]

Gepner-Puszkin

[11] Patent Number: 5,378,601
[45] Date of Patent: Jan. 3, 1995

[54] METHOD OF PRESERVING PLATELETS WITH APYRASE AND AN ANTIOXIDANT

[75] Inventor: Elena Gepner-Puszkin, New Rochelle, N.Y.

[73] Assignee: Montefiore Medical Center, Bronx, N.Y.

[21] Appl. No.: 920,191

[22] Filed: Jul. 24, 1992

[51] Int. Cl.[6] .................... A01N 1/02; C12N 9/48
[52] U.S. Cl. ............................ 435/2; 435/1; 435/212; 424/532
[58] Field of Search ............ 435/2, 1, 212, 217; 424/532

[56] References Cited

U.S. PATENT DOCUMENTS

| | | | |
|---|---|---|---|
| Re. 32,874 | 2/1989 | Rock | 424/101 |
| 4,059,967 | 11/1977 | Rowe | 62/64 |
| 4,396,716 | 8/1983 | Marconi | 435/181 |

OTHER PUBLICATIONS

Kinlough-Rathbone, Properties of Washed Platelets, Thrombos. Haemostas 1977 37 pp. 291-308.
Bode Arthur, The Use of Thrombin Inhibitors and Aprotinin Lab & Clinical Med 113 (6) Jun. 1989, pp. 753-758.
Mazoyer E., Platelet Membrane Glycoproteins . . . Throbosis Res 62, 1991, pp. 165-175.
Bode, Arthur, The Use of Inhibitors of Platelet Activation . . . Blood Cells 1992 18: 361-380.

*Primary Examiner*—Michael G. Wityshyn
*Assistant Examiner*—Ralph Gitomer
*Attorney, Agent, or Firm*—Hedman, Gibson & Costigan

[57] ABSTRACT

The invention provides a method and composition for preserving platelets which is based on the use of a composition which includes apyrase and an antioxidant. Preferred compositions will also include a protease inhibitor and optionally a solvent.

15 Claims, 3 Drawing Sheets

METHOD OF PRESERVING PLATELETS WITH APYRASE AND AN ANTIOXIDANT

BACKGROUND OF THE INVENTION

Platelet transfusion has become an integral part of the supportive care of cancer patients. Initially this was used in the treatment of patients with hematologic malignancies, but more recently, platelet transfusions have been widely used in the support of patients with solid tumors treated with high dose chemotherapy, often accompanied by autologous marrow support. Improvements in blood component separation technology have made the use of platelet concentrates more readily available. Platelet concentrates are prepared by separating platelet rich plasma (PRP) from whole blood by gentle centrifugation followed by forceful centrifugation to compact platelets into a button which is resuspended in a small volume of plasma. Platelets are normally stored at 20°–24° C. (room temperature) for up to 5 days with continuous gentle agitation in gaspermeable plastic containers. (Snyder et al. Transfusion, 26:125–30, 1986)

Platelet concentrates are now a routine by-product of the collection of red blood cells and are prepared by either pooling 6 to 8 units per adult patient or by obtaining them through the process of plateletpheresis from an individual donor. However, with either method, platelets have a brief shelf-life and the "technique" of optimal platelet storage has not been resolved.

A great deal of meticulous work has evaluated and attempted to define the optimal conditions for storage of platelets. Factors which are important include temperature, pH of the plasma, which in turn depends upon the volume of the storage bag and gas exchange across the bag surface, mode of agitation, and the presence or absence of other cells in the storage product.

The difficulty of preserving platelets for future use without degrading their activity is well recognized in the art. The loss of activity is well documented in the literature e.g., Baythoon et al, *J. Clin. Pathol.*, 35:870–874 (1982); Van Prooijen et al, *Transfusion*, 26:4 pp. 358–362; and Schiffer et al., *Thrombos. Haemostas*, 36:221–229 (1976).

During platelet preparation, platelets are activated and when stored for several days at room temperature they exhibit a variety of functional and morphological abnormalities including a poor response to aggregating agents and a lowering of the plasma pH. To maintain an acceptable pH during storage it is crucial that sufficient oxygen be able to enter the bag and that $CO_2$ be able to diffuse out. A lack of oxygen entry into the storage container causes platelets to switch from aerobic to anaerobic metabolism with a resultant increase in the production of lactic acid which in turn is accompanied by an increase in pH. Agitation during storage is also considered necessary (Koerner K. Von Sang 44:37–41, 1983; Wallvil J. et al., Transfusion 30: 639–43, 1990) and although the mechanism behind the impairment of non agitated platelets is not understood, it has been suggested that gas exchange may be of major importance.

The prior art preservation techniques have included the preparation and use of frozen autologous platelets with and without dimethyl sulfoxide. Cryopreservation has not been generally accepted for storage with the exception of locations which stockpile matched donor platelets and autologous platelets for leukemia patients. The key issue affecting acceptance is the poor quality of the units after thawing.

The use of dimethyl sulfoxide has not been completely satisfactory because of irreversible changes in the platelets. *Thrombos. Haemostas. (Stuttq.)*, 36 pp. 211–229 (1976).

Cryopreservation of platelets leads to severe reduction in the functional response of these cells. The nature of the defects underlying the deficient function of stored platelets is unclear. However, it is known that the platelets become activated during storage and it is believed that this activation induces the release of platelet ADP (adenosine diphosphate) which can cause irreversible or reversible changes in platelet membranes, thus, rendering them refractory to aggregating agents.

The applicant has discovered that if an adenosine-5'-triphosphatase and an adenosine-5'-diphosphatase is added to platelets prior to storage at room temperature with or without agitation or at cryotemperatures, the platelets have an improved response to ADP induced aggregation as compared to platelets which are stored without the additives. The invention provides for extended storage of platelets without substantial loss of activity which has been a characteristic of prior art preservation methods. The improved metabolic integrity as measured by plasma pH, $pO_2$, $pCO_2$ and hypotonic shock response (HRS) were maintained throughout the storage period.

Accordingly it is a primary object of this invention to provide a method for the preservation of platelets at room temperature (20° to 24° C.) under standard agitation conditions as employed by blood banks or without agitiation under cryopreservation temperatures. ($-70°$ C. to $-195°$ C.)

It is also an object of this invention to provide a novel composition which has special utility in the preservation of platelets.

These and other objects of the invention will be apparent from the appended specification.

SUMMARY OF THE INVENTION

The method of the invention comprises contacting platelets with an effective amount of an adenosine-5'-triphosphatase and an adenosine-5'-diphosphatase, or an enzyme having these activities and thereafter maintaining said mixture at a temperature which does not substantially affect the viability of the platelets. In a preferred embodiment of the invention an antioxidant such as ascorbic acid may be added and/or a protease inhibitor such as aprotinin may be added to the adenosine-5'-triphosphatase and adenosine-5'-diphosphatase or an enzyme having these activities. The preferred adenosine-5'-triphosphatase/adenosine-5-diphosphatase is apyrase.

DETAILED DESCRIPTION OF THE INVENTION

Figure 1:
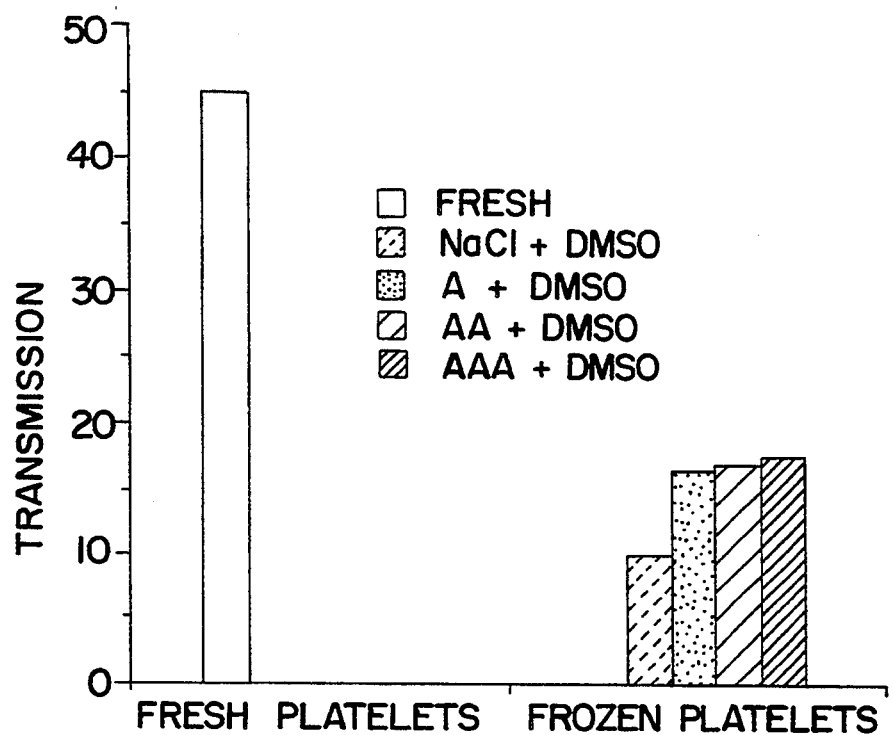
FIG. 1 is a graph which shows the relative aggregation of fresh and cryopreserved platelets collected in ACD anticoagulated according to Example 1.

Blood is collected from donors and treated using standard procedures to obtain a platelet concentrate.

An amount of adenosine-5'-triphosphatase and adenosine-5'-diphosphatase which is effective to stabilize the platelets is added to the platelets along with an effective amount of an antioxidant and a protease inhibitor which will not affect the viability of the platelets. Generally from 0.07–0.15 mg of the adenosine-5'-triphosphatase and adenosine-5'-diphosphatase, e.g. apyrase, is added to each ml of platelet concentrate.

The preferred antioxidant is ascorbic acid although other antioxidants such as α-tocopherol, β-carotene and the like which may be utilized in effective amounts. The preferred amount of ascorbic acid is from 5–15 mM of platelet concentrate.

It is preferred to add a protease inhibitor such as aprotinin to inhibit the activation of plasmin and kallikrein in the stored platelets. The aprotinin or other effective protease inhibitor may be used in an effective amount which will enhance the stability of the platelets. The preferred amount of aprotinin is from about 1.2 to about 1.5 Thrombin Inhibitor Units (TIU)(one TIU is equivalent to 550 Kalikrein International Units)(KIU) per ml of platelets.

The platelets may be stored at room temperature or frozen at $-70°$ to $-195°$ C. The convenience of storage at room temperature is readily apparent but the use of cryopreservation techniques will allow the storage of the preserved platelets for extended periods of time. Agitation may be used in conjunction with the use of room temperature storage or the platelets may be stored without agitation. It is preferred to limit room temperature storage to periods of from about 5 to 7 days in order to avoid microbial contamination which occurs during prolonged storage at room temperatures.

The apyrase alone or in combination with the antioxidant or in combination with the protease inhibitor and antioxidant may be dissolved in a diluent and the mixture added to the platelets. The diluent may be any non-toxic liquid which does not adversely interact with platelets.

For cryopreservation, dimethyl sulfoxide at a level of about 3–10% w/w based on the weight of the platelets and the preservatives may be used. In addition hydroxyethyl starch (8 to 10% in saline) may be used. For cryopreservation, the platelets may be incubated for one hour with apyrase, ascorbic acid and aprotinin prior to the addition of an equal volume of 10 percent dimethyl sulfoxide in plasma so the final concentration of dimethyl sulfoxide is 5 percent. Generally any suitable container may be used for storage under appropriate conditions but it is preferred to use the plastic freezing bags such as those which are supplied by Fenwal or ChartMed for freezing. Conventional $-70°$ C. freezers may be used or other low temperature means such as liquified gases e.g. nitrogen may be employed.

The preservatives may be separately added to the platelets in the plastic bag or they may be added in a mixture with the diluent according to the procedure set forth above.

When it is desired to reconstitute the preserved platelets for administration to a patient, the stored platelets, if necessary, should first be brought to room temperature and thereafter subjected to a washing procedure to eliminate the dimethyl sulfoxide. A water bath at 37° C. may be used to bring the platelets to room temperature. The platelets may be washed with an ABD compatible plasma, centrifuged and resuspended in plasma. This procedure removes substantially all of the apyrase, and/or the antioxidant and/or the protease inhibitor and dimethyl sulfoxide prior to the administration of the platelets to a patient.

DESCRIPTION OF THE PREFERRED EMBODIMENT

EXAMPLE 1

Platelets are taken from healthy volunteer donors by the use of Blood Cell Separator Cobe-Spectra. Whole blood is anticoagulated with acid citrate dextrose (ACD) (1:9) and after passing through the separation belt is divided into platelet concentrates, plasma and red blood cells. During this procedure, the plasma and the red blood cells are reinfused to the donor. The volume of blood proceeds depends on the pre-count of the platelets, but usually equals 2.5–3.0 liter. Platelet concentrates are continuously transferred to the collection bag to a final volume of 180 ml and centrifuged at $2000 \times g$ for 15 min at room temperature. Almost all of the platelet poor plasma is transferred into an empty plastic bag, leaving 45 ml over the platelet pellet. At this point 0.1 mg of apyrase per ml (of platelet suspension) alone or in combination with 10 mM of ascorbic acid and/or in combination with aprotinin 700 kallikren units/ml of platelet suspension are added to the bag containing the platelet pellet. The bag containing the platelets is left without any disturbance for one half hour, and then resuspended on an horizontal shaker. The platelet suspension is slowly mixed with constant agitation with 45 ml of autologous plasma containing 4.5 ml of dimethyl sulfoxide. The final concentration of dimethyl sulfoxide is 5%. Platelet concentrates are then transferred to the polyolefin plastic bag (ChartMed) and stored in a metal container which is placed horizontally into a vapor of liquid nitrogen or kept frozen at $-80°$ C.

When the platelets are required for use, the frozen platelets are taken off from the vapor phase liquid nitrogen and the metal container is removed and the bag containing the platelet concentrate is placed in a water bath at 37° C. After thawing, an equal volume of ABO compatible plasma is added to the PC prior to centrifugation at $2000 \times g$ for 15 minutes. The platelet pellet is then resuspended in ABO compatible plasma without apyrase, ascorbic acid, aprotinin and dimethyl sulfoxide.

It is known that platelet count recovery in vitro after freezing in the presence of dimethyl sulfoxide is about 90% and after washing them is about 75–80% indicating that platelet damage occurs during their manipulation.

Platelet aggregation in 0.5 ml of the reconstituted platelet suspension was recorded at 37° C. with an aggregometer (Payton Associates, Buffalo, N.Y.). Platelet suspension, $300-400 \times 10^3$ per $\mu l$, was stirred for 30 seconds before the addition of 40 $\mu M$ adenosine diphosphate and the reaction allowed to continued for 4 minutes. The results are shown in FIG. 1. The reduction of the platelet response is expressed as the percentage decrease in maximal light transmission of the fresh non-frozen platelets which has been subjected to two cycles of centrifugation compared to thawed dimethyl sulfoxide-treated platelets in the absence or presence of apyrase alone (A) or in conjunction with ascorbic acid (AA) or in combination with apyrase, ascorbic acid and aprotinin (AAA).

The aggregation response of fresh platelets, which were subjected to two steps of centrifugation, to 40 μM adenosine diphosphate resulted in 45% increase in light transmission. In general, the process of freezing, thawing and washing resulted in decreased platelet response to adenosine diphosphate. However, as depicted in FIG. 1, platelets stored only in dimethyl sulfoxide retained minimal response. Addition of apyrase alone (A), or with ascorbic acid (AA) or with ascorbic acid and aprotinin (AAA) prior to freezing substantially improved platelet response to adenosine diphosphate induced aggregation.

Platelet Hypotonic Shock response is a measurement of the platelet resistance to cell damage. Restoration of platelets after hypotonic shock is an indicator of platelet recovery after transfusion. The apyrase treated platelets maintain their response to hypotonic shock as well as the platelets which are treated with dimethyl sulfoxide alone.

EXAMPLE 2

Figure 2:
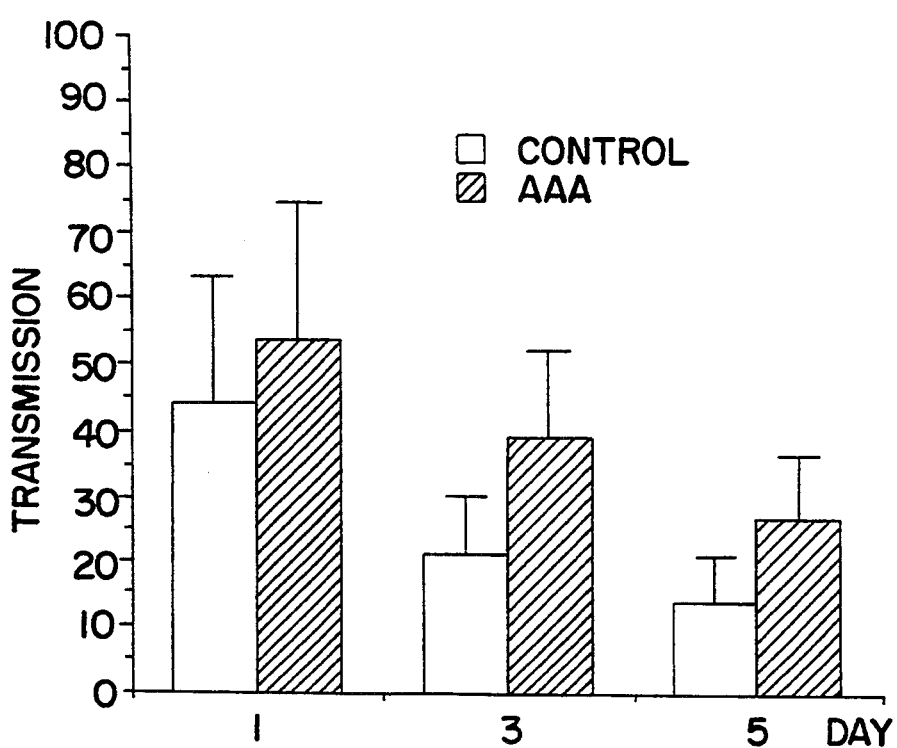
FIG. 2 is a graph which shows the relative aggregation of platelets collected in CPDA-1 anticoagulant stored for 5 days at room temperature.
Figure 3:
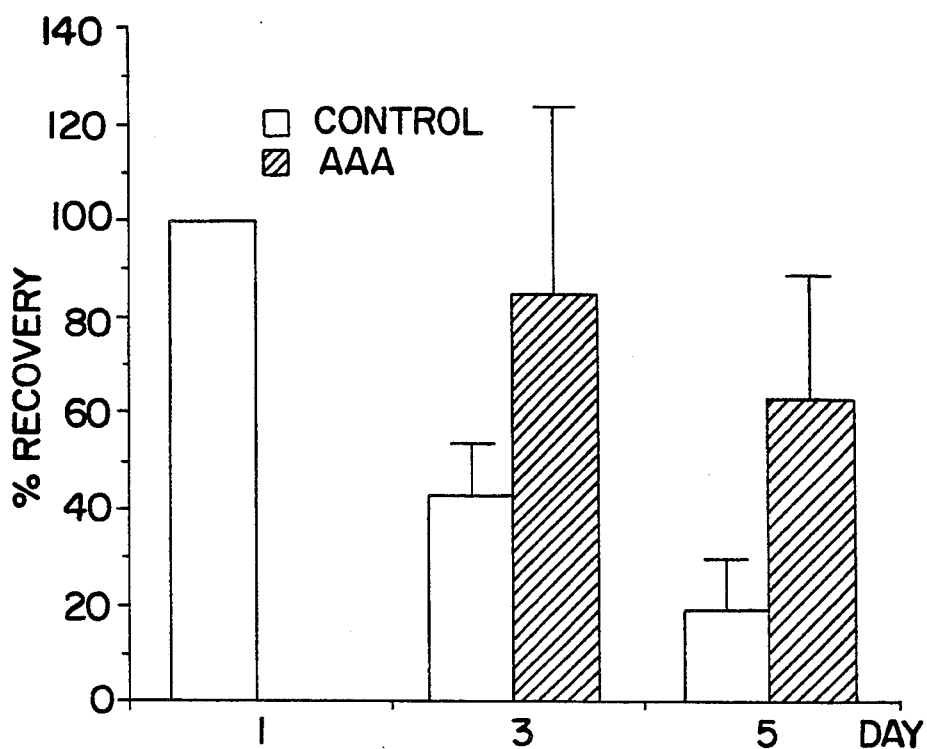
FIG. 3 is a graph which shows the relative recovery of platelet aggregation for platelets which were stored at room temperature for 5 days.

Platelets purchased from the Bergen Community Blood Bank were obtained from healthy volunteers by manual separation of whole blood or by the use of an automatic blood cell separator using CPDA-1 (citrate-phosphate-dextrose-adenine) (1:9) as an anticoagulant. After differential centrifugation, the platelet pellets stored in Fenwal PL 1240 bags are resuspended in 60 ml of autologous plasma and placed for 24 hours on a rotator at 6 rpm. The resuspended platelets were diluted with another 60 ml of autologous plasma and equal volumes of 60 ml were separated into two plastic bags (Cutter CLX). The control bag received one ml of saline while the test bag contained one ml of a mixture of 0.1 mg of apyrase per ml of platelet concentrate, 10 mM of ascorbic acid and 700 Kalikrein units of aprotinin per ml of platelet concentrate in normal saline. The bags were placed on a rotator for 24 hours at 6 rpm. After one hour of incubation at room temperature with rotational agitation, four ml of the mixture was removed from each bag. Platelet function and integrity was assessed using the following parameters: (a) platelet aggregation induced by adenosine diphosphate (ADP); (b) pH; (c) $pO_2$ consumption; (d) $pCO_2$ production and (e) hypotonic shock response (HSR). The remaining samples were tested again at day 3 and at day 5. FIG. 2 shows the response of the platelets to 40 μM ADP induced aggregation at day 1, 3, and 5. Platelet aggregation was measured in a dual-channel aggregometer (Payton Scientific, Buffalo, N.Y.). The beneficial effect of apyrase is seen as early as one hour after incubation, however it is more evident at days 3 and 5. If the ADP induced response of fresh platelets is used as a baseline of 100 percent, the recovery of cell function in the apyrase-treated platelets at day 3 and day 5 is 85 percent and 60 percent respectively while the saline treated samples were at a level of 40 and 20 percent respectively (FIG. 3).

Platelet integrity as measured by plasma pH; $pO_2$ (mmHg); and $pCO_2$ (mmHg) were determined at 22° C. on a blood gas analyzer (ABL Model 30 Radiometer, Copenhagen, Denmark). The results are shown in Table 1. The level of platelet integrity was maintained within acceptable limits during the five (5) day storage period. The hypotonic shock response recovery tests were performed by adding 250 μl deionized water to a 500 μl platelet suspension in a dual channel aggregometer (Payton Scientific, Buffalo, N.Y.) at room temperature without stirring. As shown in Table 1, no major changes were observed during a five day period and the HSR was maintained between 50 and 60%.

TABLE 1

Evaluation of the effect of AAA on platelet integrity and respiration after storage at room temperature

| | pH | $pO_2$ | $pCO_2$ | HSR |
|---|---|---|---|---|
| Day 1 | | | | |
| Control | 7.424 ± 0.034 | 42.93 ± 11.2 | 20.9 ± 1.51 | 60.0 ± 6.11 |
| AAA | 7.327 ± 0.043 | 33.71 ± 10.5 | 24.5 ± 2.39 | 55.1 ± 9.59 |
| Day 3 | | | | |
| Control | 7.535 ± 0.144 | 74.86 ± 14.13 | 10.9 ± 0.88 | 60.2 ± 14.35 |
| AAA | 7.468 ± 0.135 | 55.84 ± 20.52 | 11.9 ± 1.18 | 59.5 ± 14.02 |
| Day 5 | | | | |
| Control | 7.337 ± 0.362 | 57.38 ± 28.49 | 8.08 ± 1.45 | 54.8 ± 14.00 |
| AAA | 7.323 ± 0.292 | 52.68 ± 23.68 | 8.67 ± 1.54 | 43.6 ± 11.15 |

Figure 4:
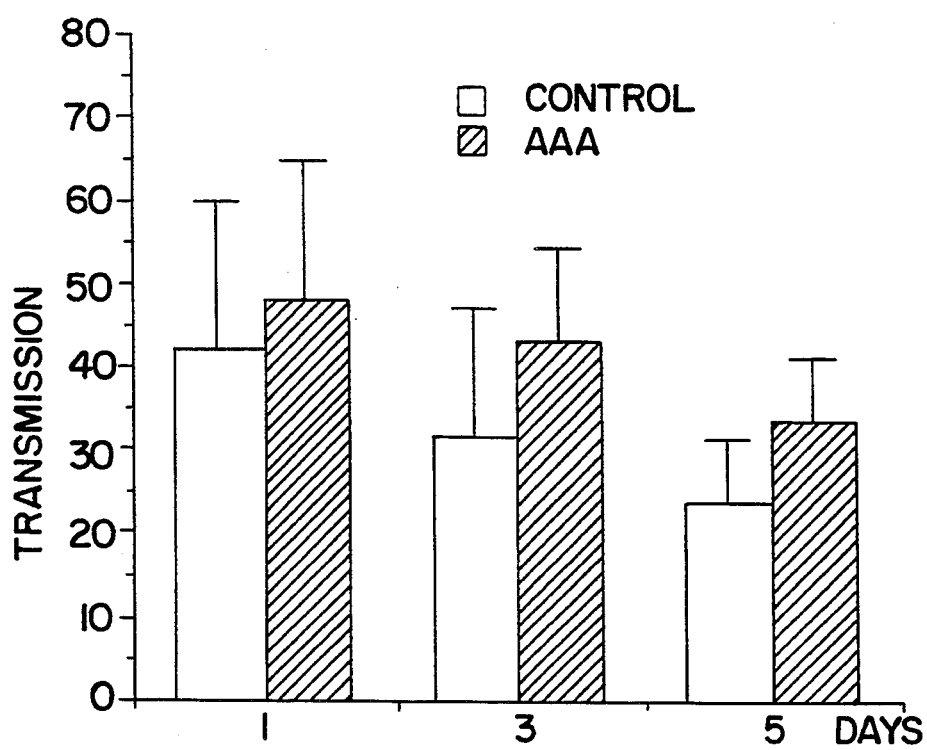
FIG. 4 is a graph which shows the relative aggregation of platelets collected in CPDA-1 anticoagulant maintained and stored without agitation for five days at room temperature.

Studies at room temperature were also performed as described above with the exception that platelets were not rotated and were kept non-agitated for 5 days. Platelet aggregation was measured at days 1, 3 and 5 and as depicted in FIG. 4, samples containing AAA had improved response to ADP. The control contained platelets treated with 1 ml of saline.

Figure 5:
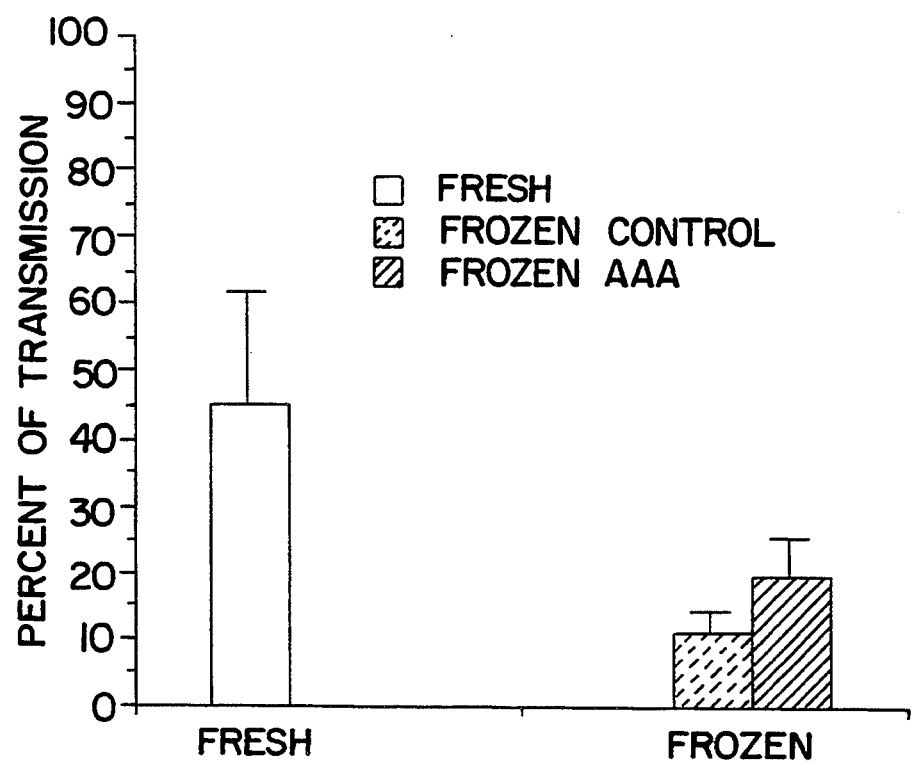
FIG. 5 is a graph which shows the relative aggregation of fresh and cryopreserved platelets collected in CPDA-1 anticoagulant.
Figure 6:
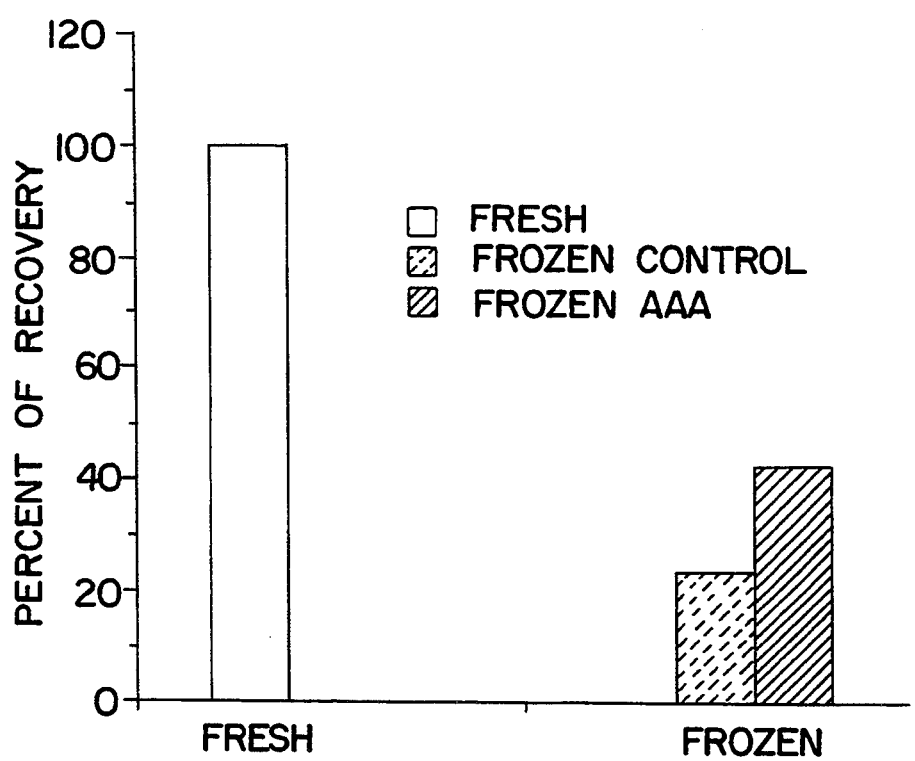
FIG. 6 is a graph which shows the recovery of aggregation platelets after freezing.

The effect of the use of apyrase, ascorbic acid and aprotinin on ADP induced aggregation of the cryo-preserved platelets (stored at −80° C.) is substantially improved. FIG. 5 shows that while thawed control samples maintained at an approximately 11%±3.1% of the aggregating response, thawed platelets treated with apyrase, ascorbic acid and aprotinin were at a level of 20%±6%. Recovery of platelet aggregation as compared to fresh platelets (100%) was 24% for untreated samples versus 43% on apyrase, ascorbic acid and aprotinin treated sample (FIG. 6). This represents an improvement on the thawed apyrase, ascorbic acid and aprotinin treated samples of 78%. Although, this level of response does not reach the values of samples stored at room temperature, the advantage of storing platelets for long periods of time is very valuable especially when autologous platelet transfusion is required.

While the present invention has been explained in relation to its preferred embodiment, it is to be understood that various modifications thereof will be apparent to those skilled in the art upon reading this specification. Therefore, it is to be understood that the invention disclosed herein is intended to cover all such modifications as fall within the scope of the appended claims.

I claim:
1. A method for the preservation of human blood platelets which consists essentially of:
   (a) adding an effective amount of an adenosine-5'-triphosphatase and an adenosine-5'-diphosphatase enzyme or an enzyme having activity of both adenosine-5'-triphosphatase and adenosine-5'-diphosphatase. which does not adversely affect platelets in a diluent, to platelets to form a mixture;

(b) adding an antioxidant to the mixture of step(a); and (c) maintaining the mixture of step (b) at a temperature which does not affect the viability of the platelets.

2. A method for the preservation of human blood platelets as defined in claim 1 wherein the antioxidant is ascorbic acid.

3. A method for the preservation of human blood platelets as defined in claim 1 wherein a protease inhibitor is added to step (a).

4. A method for the preservation of human blood platelets as defined in claim 1 wherein the adenosine-5'-triphosphatase and adenosine-5'-diphosphatase is apyrase.

5. A method for the preservation of human blood platelets as defined in claim 1 wherein the temperature is between 20° to 24° C.

6. A method for the preservation of human blood platelets as defined in claim 1 wherein the temperature is between −70° to −195° C.

7. A method for the preservation of human blood platelets which consists essentially of the steps of:

(a) obtaining platelets from a donor;

(b) concentrating the platelets;

(c) adding from 0.07 to 0.15 mg of apyrase per ml of platelets, from 1.2 to 1.5 Thrombin Inhibitor Units of aprotinin and 5-15 mM of ascorbic acid dissolved in saline or in plasma to the platelets of step (b) to form a platelet suspension;

(d) adding to the platelet suspension of step (c) a mixture of autologous plasma and dimethyl sulfoxide in a sufficient amount so that the final concentration is 5% dimethyl sulfoxide; and (e) maintaining the product of step (d) at a temperature of about −70° C. to −195° C.

8. A preserved platelet concentrate which comprises:

(a) a platelet concentrate;

(b) an amount of apyrase which is effective for platelet preservation;

(c) an amount of an antioxidant which is effective for platelet preservation; and (d) an amount of a protease inhibitor which is effective for platelet preservation.

9. A preserved platelet concentrate as defined in claim 8 wherein the antioxidant is ascorbic acid and dimethyl sulfoxide is added as a diluent.

10. A preserved platelet concentrate as defined in claim 9 wherein the protease inhibitor is aprotinin.

11. A preserved platelet concentrate as defined in claim 9 which also includes a solvent.

12. A composition for preserving platelets which consists essentially of:

(a) an effective amount of apyrase;

(b) an effective amount of an antioxidant; and (c) a diluent

13. A composition for preserving platelets as defined in claim 12 which also includes a protease inhibitor.

14. A preserved platelet concentrate as defined in claim 13 which includes the solvent dimethyl sulfoxide.

15. A composition as defined in claim 13 wherein the protease inhibitor is aprotinin.

* * * * *